(12) United States Patent
Kappock et al.

(10) Patent No.: US 9,540,520 B2
(45) Date of Patent: Jan. 10, 2017

(54) SYNTHESIS OF COPPER PYRITHIONE FROM ZINC PYRITHIONE AND COPPER COMPOUND

(75) Inventors: Paul S. Kappock, Cumming, GA (US); Robert J. Martin, Asheville, NC (US)

(73) Assignee: Arch Chemicals, Inc., Atlanta, GA (US)

( * ) Notice: Subject to any disclaimer, the term of this patent is extended or adjusted under 35 U.S.C. 154(b) by 109 days.

(21) Appl. No.: 14/239,203

(22) PCT Filed: Aug. 17, 2012

(86) PCT No.: PCT/US2012/051251
§ 371 (c)(1),
(2), (4) Date: May 16, 2014

(87) PCT Pub. No.: WO2013/025960
PCT Pub. Date: Feb. 21, 2013

(65) Prior Publication Data
US 2014/0296371 A1    Oct. 2, 2014

Related U.S. Application Data

(60) Provisional application No. 61/524,494, filed on Aug. 17, 2011.

(51) Int. Cl.
*C07D 213/89* (2006.01)
*C08K 5/3432* (2006.01)
(Continued)

(52) U.S. Cl.
CPC .............. *C09D 5/1625* (2013.01); *A01N 59/20* (2013.01); *C07D 213/89* (2013.01); *C08K 5/3432* (2013.01); *Y10T 428/2982* (2015.01)

(58) Field of Classification Search
CPC ....... C07D 213/89; C08L 43/04; C08K 5/3432
See application file for complete search history.

(56) References Cited

U.S. PATENT DOCUMENTS 3,615,744 A   10/1971   Yokoo et al.
4,396,766 A   8/1983    Farmer et al.
(Continued)

FOREIGN PATENT DOCUMENTS

CN   1258687   7/2000
CN   1544541   11/2004
(Continued)

OTHER PUBLICATIONS

Nakajima et al., "High performance liquid chromatographic determination of zinc pyrithione in antidandruff preparation based on copper cheiate formation." (1990). Journal of Chromatography, vol. 502, is. 2, p. 379-384.
(Continued)

*Primary Examiner* — Brieann R Fink
(74) *Attorney, Agent, or Firm* — Dority & Manning, P.A.

(57) ABSTRACT

A composition containing unique particles of copper pyrithione wherein greater than 20 wt % to 90 wt % of the particles have a particle size of greater than 10 microns, as determined by laser light scattering using a particle size distribution analyzer, and wherein the particles are flat acicular needle-shaped is described herein. Also described herein is an antifouling paint containing the copper pyrithione and a method of making the composition and antifouling paint.

7 Claims, 1 Drawing Sheet

(51) Int. Cl.
*C09D 5/16* (2006.01)
*A01N 59/20* (2006.01)

(56) References Cited

U.S. PATENT DOCUMENTS

| | | | |
|---|---|---|---|
| 4,774,080 A | 9/1988 | Yamamori et al. |
| 4,918,147 A | 4/1990 | Yamamori et al. |
| 5,057,153 A | 10/1991 | Ruggiero |
| 5,080,892 A | 1/1992 | Yamamori et al. |
| 5,098,473 A | 3/1992 | Hani et al. |
| 5,112,397 A | 5/1992 | Farmer et al. |
| 5,137,569 A | 8/1992 | Waldron et al. |
| 5,185,033 A | 2/1993 | Hani et al. |
| 5,232,493 A | 8/1993 | Waldron et al. |
| 5,238,490 A | 8/1993 | Farmer et al. |
| 5,246,489 A | 9/1993 | Farmer et al. |
| 5,252,123 A | 10/1993 | Hani et al. |
| 5,298,061 A | 3/1994 | Waldron et al. |
| 5,342,437 A | 8/1994 | Gavin et al. |
| 5,540,860 A | 7/1996 | Hosseini et al. |
| 5,650,095 A | 7/1997 | Hosseini et al. |
| 5,880,173 A | 3/1999 | Matsuda et al. |
| 6,017,562 A | 1/2000 | Kaufman et al. |
| 6,110,990 A | 8/2000 | Nakamura et al. |
| 6,162,446 A | 12/2000 | Hani et al. |
| 6,172,132 B1 | 1/2001 | Nakamura et al. |
| 6,177,530 B1 | 1/2001 | Sugihara et al. |
| 6,242,007 B1 | 6/2001 | Mohseni et al. |
| 6,248,806 B1 | 6/2001 | Codolar et al. |
| 6,432,432 B1 | 8/2002 | Mohseni et al. |
| 6,458,878 B1 | 10/2002 | Tsuboi et al. |
| 6,821,326 B2 | 11/2004 | Waldron et al. |
| 7,022,750 B2 | 4/2006 | Camp et al. |
| 7,335,248 B2 | 2/2008 | Abou-Nemeh |
| 7,435,771 B2 | 10/2008 | Lei et al. |
| 7,455,851 B1 | 11/2008 | Nelson et al. |
| 7,481,873 B2 | 1/2009 | Waldron et al. |
| 7,544,367 B2 | 6/2009 | Mohseni et al. |
| 7,659,397 B2 | 2/2010 | Hidaka |
| 7,691,938 B2 | 4/2010 | Finnie |
| 7,942,958 B1 | 5/2011 | Gavin et al. |
| 8,541,493 B2 | 9/2013 | Kappock et al. |
| 2002/0110575 A1 | 8/2002 | Gavin et al. |
| 2002/0197283 A1 | 12/2002 | Mohseni et al. |
| 2003/0207962 A1* | 11/2003 | Oya ............. C09D 143/00 523/177 |
| 2003/0215522 A1 | 11/2003 | Johnson et al. |
| 2004/0058855 A1 | 3/2004 | Schwartz et al. |
| 2004/0118319 A1 | 6/2004 | Waldron et al. |
| 2004/0191331 A1 | 9/2004 | Schwartz et al. |
| 2005/0065232 A1 | 3/2005 | Okimoto et al. |
| 2005/0252408 A1 | 11/2005 | Richardson et al. |
| 2006/0148977 A1 | 7/2006 | Finnie |
| 2007/0110700 A1 | 5/2007 | Wells et al. |
| 2007/0117895 A1 | 5/2007 | Lei et al. |
| 2007/0207178 A1 | 9/2007 | Waldron et al. |
| 2008/0124298 A1 | 5/2008 | Solomon et al. |
| 2009/0053166 A1 | 2/2009 | Nimoto |
| 2009/0215739 A1 | 8/2009 | Mohseni et al. |
| 2010/0021530 A1 | 1/2010 | Weinfield |
| 2010/0028391 A1 | 2/2010 | Okawa et al. |
| 2010/0278876 A1 | 11/2010 | Doumae et al. |
| 2011/0206632 A1 | 8/2011 | Kappock et al. |
| 2013/0183362 A1 | 7/2013 | Kappock et al. |

FOREIGN PATENT DOCUMENTS

| | | | |
|---|---|---|---|
| CN | 102869257 | 1/2013 | |
| EP | 1695963 | 8/2006 | |
| EP | 2204423 | 7/2010 | |
| KR | EP 1695963 A1 * | 8/2006 | ............ A01N 55/02 |
| WO | 90/47372 | 10/1998 | |
| WO | 2005/075582 | 8/2005 | |
| WO | 2007/074656 | 7/2007 | |
| WO | 2007/103013 | 9/2007 | |
| WO | 2008/038967 | 4/2008 | |
| WO | 2009/031509 | 3/2009 | |

OTHER PUBLICATIONS

International Search Report and Written Opinion for PCT/US2012/051251, Nov. 28, 2012.
International Preliminary Report on Patentability and International Search Report fo PCT/US2011/023865, Aug. 21, 2012.
EP Search Report and Opinion for EP 11745044, Jul. 30, 2013.

* cited by examiner

SYNTHESIS OF COPPER PYRITHIONE FROM ZINC PYRITHIONE AND COPPER COMPOUND

This application claims the benefit of priority under 35 USC §119(e) to U.S. provisional patent application Ser. No. 61/524,494 filed on Aug. 17, 2011, entitled "SYNTHESIS OF COPPER PYRITHIONE FROM ZINC PYRITHIONE AND COPPER COMPOUND".

FIELD OF INVENTION

The present invention relates to unique particles of copper pyrithione formed by reacting zinc pyrithione and a copper compound in the presence of a polymer matrix. The present invention also relates to compositions containing such copper pyrithione particles.

BACKGROUND OF THE INVENTION

Ships, fishnets or other underwater structures or equipment tends to be attacked aquatic organisms such as barnacles, mussels, and algae, and the like. Organisms can grow and multiply and eventually cause significant problems. For example, in the case of a ship's hull, the growth of marine organisms on the hull can increase the frictional resistance between the hull and water, thus increasing fuel consumption and reducing the speed of the ship.

One approach to the problems is to coat the surfaces of the structures with an antifouling coating which contains a "self-polishing" polymer is present. "Self-polishing" polymers generally have hydrolysable groups within the polymer backbone. Over time, the polymer at the outmost layer of the coating is hydrolyzed and becomes water erodible residue. This water erodible residue is subsequently removed by water, resulting in a smooth, foul free surface. Such action is commonly referred to as a "self-polishing" effect, which continues until the antifouling coating is removed from the surface to which it is coated. At which time, a new anti-fouling coating must be placed on the surface. Generally, self-polishing polymers are typically acrylates with metal ester or silyl ester functionality.

Self-polishing polymers can be used in combination with biocides such as copper pyrithione to further enhance anti-fouling performance. Copper pyrithione utilized in the paints typically have relatively small particle sizes. Illustratively, EP 1 695 963 B1 discloses that if more than 20% of the copper pyrithione particles have a size of over 10 micron, then it is difficult to disperse the particles in a paint.

Unfortunately, in some formulations, copper pyrithione of a small particle size may leach out of the paint film too fast, particularly in warm water, thus compromising the antimicrobial efficacy of the paint.

Accordingly, there is a need in the paint manufacturing community to provide a paint that contains adequately dispersed copper pyrithione particles having larger particle sizes relative to conventional copper pyrithione particles utilized in the paint. The present invention provides an answer to that need.

SUMMARY OF THE INVENTION

In one aspect, the present invention provides a composition containing unique particles of copper pyrithione wherein greater than 20 wt % to 90 wt % of the particles have a particle size of greater than 10 microns determined by laser light scattering using a particle size distribution analyzer, and wherein the particles are flat acicular needle-shaped.

In another aspect, the present invention relates to a process for the synthesis of the unique particles of copper pyrithione described above. The process comprises reacting zinc pyrithione and a copper compound such as copper hydroxide in a non-reactive polymer matrix. The particles are formed "in situ" resulting in much less agglomeration of the particles than if made in the conventional manor. Safety in handling is an added benefit because there is no dusting when adding the copper pyrithione into a paint. Further the copper pyrithione particles of the invention can be easily mixed into a paint because they are already pre-dispersed in the non-reactive polymer when they are formed.

In yet another aspect, the present invention relates to an antifouling coating composition containing copper pyrithione particles and silyl acrylate wherein from 20 wt % to 90 wt % of the particles based on the total weight of copper pyrithione have a size of greater than 10 microns determined by laser light scattering using a particle size distribution analyzer, and wherein the particles are flat acicular needle-shaped. The coating composition of the invention contains a higher percentage of copper pyrithione particles have a size of greater than 10 microns compared with convention copper pyrithione particles. The larger particles will remain in the paint film for a longer time and it is expected that the coating composition of the invention has sustained antifouling effect and is particularly beneficial in warm water.

These and other aspects will become apparent when reading the detailed description of the invention.

DETAILED DESCRIPTION OF THE PREFERRED EMBODIMENTS

Figure 1:
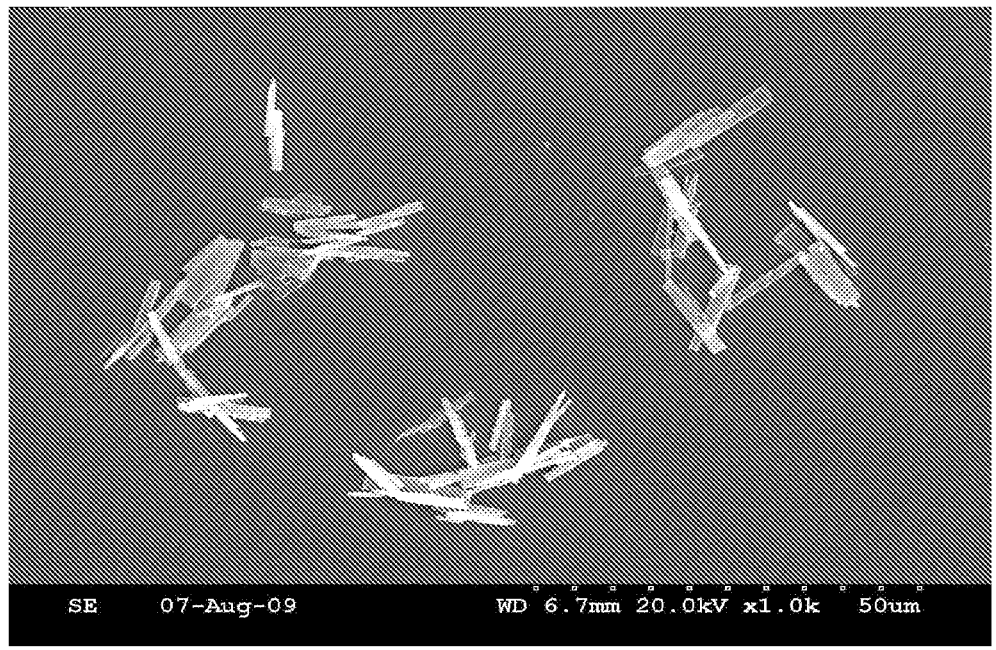
FIG. 1 is a micrograph of the copper pyrithione of the present invention.

It has now been surprisingly found that copper pyrithione particles having a unique shape and size distribution are formed when zinc pyrithione and a copper compound are brought into contact with each other and reacted in a non-reactive polymer matrix. By "non-reactive polymer matrix" it is intended to mean a polymer matrix which does not react with either the zinc pyrithione or the copper compound. Examples of these polymer matrixes are given below. The formed copper pyrithione particles have a flat acircular needle shape. By "flat acircular needle shape" it is intended that the particles have a length, a width and a thickness wherein the length is greater than the width and the width is greater than the thickness. The flat acircular needle shape is a shape that is distinctly different from that of milled copper pyrithione.

It has also been discovered that anti-fouling paints containing the copper pyrithione of the present invention have a better resistance to cracking that conventional copper pyrithione.

The copper pyrithione particle have an average aspect ratio, defined as the length of a copper pyrithione particle divided by the width of that particle, in the range of about 5 to about 20 or more. More particularly, the average aspect ratio is in the range of 5 to about 15. Aspect ratio can be determined using any technique known to those skilled in the art, including superimposing a micron scale over particle size images ad comparing the length and width of the particle to the scale. The average aspect ratio is determined by determining the number of particles provided in the particle size image, determining the aspect ratio for each particle and mathematically determining the average of the measured aspect ratios for the particle in the image. Images of the particle may be obtained using a scanning electron microscope. Advantageously, at least 5% of the particles have an average width of about 4 to 5 microns and a length of over 20 microns.

In addition to the unique shape, the copper pyrithione particles of the invention also have a unique size distribution. In one embodiment, from 20 wt % to 90 wt %, advantageously from about 25 to about 70 wt %, more advantageously from about 30 to about 60% of the particles based on the total weight of copper pyrithione have a particle size of greater than 10 microns, as measured by laser light scattering using a particle size distribution analyzer. For example, the particle size of the copper pyrithione may be measured using a Horiba LA-910 or LA-920 particle size distribution analyzer. In addition, the samples of the copper pyrithione may be sonicated in an aqueous solution before the particle size is measured.

The copper pyrithione particles made according to the present invention are less likely to agglomerate or settle, as compared with commercially-available milled copper pyrithione. Without being bound by any particular theory, it is hypothesized that the copper pyrithione particles are "wet out" by the polymer as they are formed during the process of the invention, thus minimizing the agglomeration and aggregation of the particles due to van der Waal forces. In addition, since copper pyrithione particles of the invention are pre-dispersed in the polymer as they are formed, they are present in a form that is suitable for incorporation into a coating composition.

Exemplary copper compounds that may be used in the present invention include copper salts, copper carboxylates, copper hydroxide, elemental copper and combination thereof. Exemplary copper salts include, for example, copper carbonate, copper nitrate, copper sulfate, copper chloride and mixtures thereof. Exemplary copper carboxylates include, for example copper acetate, copper naphthenate, copper quinolinolate, copper stearate, copper benzoate, copper ethylhexanoate, copper rosinate, and combinations thereof. In one particular embodiment, the copper compound is copper hydroxide. When copper hydroxide is employed as the copper compound reactant, zinc hydroxide particles are also formed. Not wishing to be bound by theory, it is believed that the zinc hydroxide particles, to be "wet out" by the polymer particles, thus minimizing the risk of particle agglomeration that otherwise might occur.

The form of zinc pyrithione used in the reaction is not particularly limited. For example, zinc pyrithione can be used in the form of an unmilled wet cake. This provides cost savings for a commercial process based on the present invention that does not require a milling step. Methods to produce zinc pyrithione are known to those skilled in the art. One example of preparing zinc pyrithione is described in U.S. Pat. No. 4,396,766, which is hereby incorporated by reference in its entirety.

Accordingly, in one embodiment, the present invention provides a composition of copper pyrithione particles as described above. The composition may additionally contain a polymer which is non-reactive with the zinc pyrithione and/or the copper compound. Suitable polymers include, for example, silyl acrylates, metal acrylates, such as zinc acrylates, copper acrylates, polyvinyl chloride, copolymers of vinyl chloride, vinyl acetate, copolymers of vinyl acetate, acrylic copolymers, epoxy, alkyd, polyvinyl alcohol, cellulose ethers, acid functional acrylates, chitosan, polyvinyl ethers and combinations thereof or a non-polymer binder selected from the group consisting of rosin, rosin derivatives, and combinations thereof.

Advantageously, the polymer is silyl acrylate. In one embodiment, the silyl acrylate has a number average molecular weight of from about 2000 to about 6000. Other suitable silyl acrylates are not particularly limited and are described, for example, in U.S. Pat. Nos. 6,458,878, 4,593, 055, 4,898,895 and 4,977,989, the contents of these patents are incorporated herein by reference in their entirety.

It is appreciated that non polymer binders such as rosin and rosin derivatives may also be used. Exemplary rosin derivatives include, but are not limited to, copper rosinate and rosin ester.

In another embodiment, the present invention provides a process for preparing copper pyrithione particles. The process includes reacting zinc pyrithione with a copper compound in the presence of a non-reactive polymer matrix.

Typically, the reaction may be carried out in the presence of a solvent. Preferably, the solvent contains at least a water miscible component so that if wet cake is used, the water from the zinc pyrithione wet cake is miscible with the polymer solution. If a water free polymer solution is desired, then dry powder can be used and there is no need for a water miscible solvent. In some embodiments, the solvent mixture contains a water miscible and a water immiscible component. Exemplary water miscible component includes, but is not limited to methoxy propanol, methoxy butanol, methoxy-methylethoxy propanol, butoxy ethanol, ethoxy ethanol, and porpanol. Exemplary water immiscible component includes, but is not limited to, xylene, toluene, ethyl benzene, naphthas, methyl isobutyl ketone, and cumene. Partially water miscible solvents such as methyl ethyl ketone or butanol may also be used. An exemplary solvent suitable for use in the process of the present invention is a combination of methoxy propanol and xylene. A water miscible solvent does not have to be used, but is optional.

The reaction can be conducted at room temperature or at elevated temperatures and under normal atmospheric pressure. In one embodiment, about one mole of zinc pyrithione is reacted with about one mole of copper compound to produce about one mole of copper pyrithione. The reaction is carried out in a mixture of solvent and the non-reactive polymer such as the silyl acrylate polymer.

In yet another embodiment, the present invention provides an antifouling coating composition containing copper pyrithione particles and silyl acrylate polymer described above wherein from 20 wt % to 90 wt % of the particles based on the total weight of copper pyrithione have a size of greater than 10 microns determined by laser light scattering using a particle size distribution analyzer such as Horiba LA-910 or LA-920, and wherein the particles are flat acicular needle-shaped.

Advantageously, silyl acrylate polymer and copper pyrithione combined are present in an amount of from about 10% to about 80%, more preferably from about 30% to about 60%, based on the total weight of the coating composition.

The anti-fouling coating composition of the invention may additionally contain one or more water soluble resins or slightly water soluble resins such as rosin, polyvinyl ether, chitosan, or combinations thereof. The formulating amount of these resins is preferably within the range of 1-20%, more preferably 4-15%, based on the total weight of the coating composition.

The anti-fouling coating composition may also include some other additives. For example, toxins to prevent hard fouling such as copper metal, cuprous oxide, copper thiocyanate, zinc oxide, zinc borate, barium metaborate, triphenly boron pyridine, triphenyl boron octidecyl amine, tralopyril, chlorfenapyr, tolylfluanid, or dichlofluanid; and toxins to control soft fouling such as zinc pyrithione, copper pyrithione, 4,5-dichloro-2-n-octyl-4-isothiazolin-3-one, 2-methylthio 4-tert-butyl amino-6-cyclopropyamino-s-triazine, zineb, ziram, polycarbamate, maneb, chlorothalonil, and any mixtures thereof.

Zinc oxide is typically used in conjunction with cuprous oxide in antifouling paints for the purpose of providing inhibition of hard fouling. However, since zinc oxide converts to zinc hydroxide under alkaline conditions such as in sea water, the present inventor believes that it is actually zinc hydroxide that is inhibiting the growth of hard fouling. Unfortunately, zinc oxide is typically hard to disperse in paints, although it must be well dispersed so that the paint is not gritty. This process of dispersing zinc oxide to fine particles in a paint to can take a long time. The present invention overcomes that obstacle by providing zinc hydroxide "in situ' as fine particles not in need of further dispersion.

The antifouling coatings according to the present invention can be prepared, for example, by adding resins and/or other toxins to a composition containing silyl acrylate polymer and particulate copper pyrithione having a large flat particle. The antifouling coating forms a dry film when it is coated on the substrate surface by a conventional technique and the solvent thereof is evaporated off at atmospheric temperature or elevated temperature.

The present invention is further described in detail by means of the following Examples. All parts and percentages are by weight and all temperatures are degrees Celsius unless explicitly stated otherwise.

EXPERIMENTAL

Example 1

Preparation of a Composition Containing Self-Polishing Silyl Acrylate Polymer and Copper Pyrithione A. Preparation of Silyl Acrylate Copolymer To a one liter reaction flask equipped with an addition funnel, a reflux condenser, a stirrer and a thermometer, were added 368.0 grams of xylene. The reaction mixture was brought up to 95±5° C. while stirring at low speed under a nitrogen blanket.

The following monomers and initiators were premixed thoroughly in a separate flask: 180.0 grams of methyl methacrylate, 20.0 grams of 2-methyl ethyl acrylate, 200.0 grams of triisopropyl silyl acrylate, and 4.0 grams of 2,2-azobis(2-methylbutanenitrile. The monomer/initiator mixture was transferred to the addition funnel mounted on the reaction flask; and was added at a constant rate to the reaction flask over a period of 3 hours at 95±5° C. while stirring continuously for an additional 2 hours.

Next, the addition funnel was charged with premixed xylene (32.0 grams) and t-butylperoxy 2-ethylhexyl carbonate (2.0 grams). This chaser mixture was added into the reaction flask drop wise over the course of one half hour at 95±5° C. The reaction mixture was stirred for an additional 1½ hours at 95±5° C. thus obtaining the silyl acrylate polymer.

The molecular weight of the above polymer measured by Gel Permeation Chromatography is typically approximately Mw=17,000 and Mn=4700. Viscosity of the silyl acrylate in 50% xylene is typically about 3,000 cps (#4 LV spindle at 12 rpm).

B. Preparation of a Composition Containing Silyl Acrylate Polymer and Copper Pyrithione To a ½ pint mixing vessel was added 93.0 grams of the silyl acrylate polymer solution prepared in section A. The mixing vessel was placed under a high speed cowles type disperser with a 1' blade. The mixer was turned to 1000 rpm. To the mixing vessel were added 25.9 grams of 60% solids zinc pyrithione wet cake and 26.3 grams of methoxypropanol. The speed of the mixer was increased to 2000 rpm. To the mixing vessel, was added 1.45 grams of copper hydroxide (58% copper), followed by 10 minutes of mixing and succeeding addition of three more batches of copper hydroxide (1.45 grams each batch). Once the reaction mixture had turned a dark green color, 2.50 grams of $NH_4OH$ (29.6%) was added to the mixing vessel and the stirring was continued for 30 minutes to provide a composition containing silyl acrylate polymer and copper pyrithione.

Example 2 and Comparative Example A
Microscopic Analysis of Copper Pyrithione

Example 2

Microscopic images of copper pyrithione formed from example 1 was shown in FIG. 1. Scale on bottom right is 0-50 microns. The SEM shows the copper pyrithione particles of the present invention to be flat acicular needles.

Figure 2:
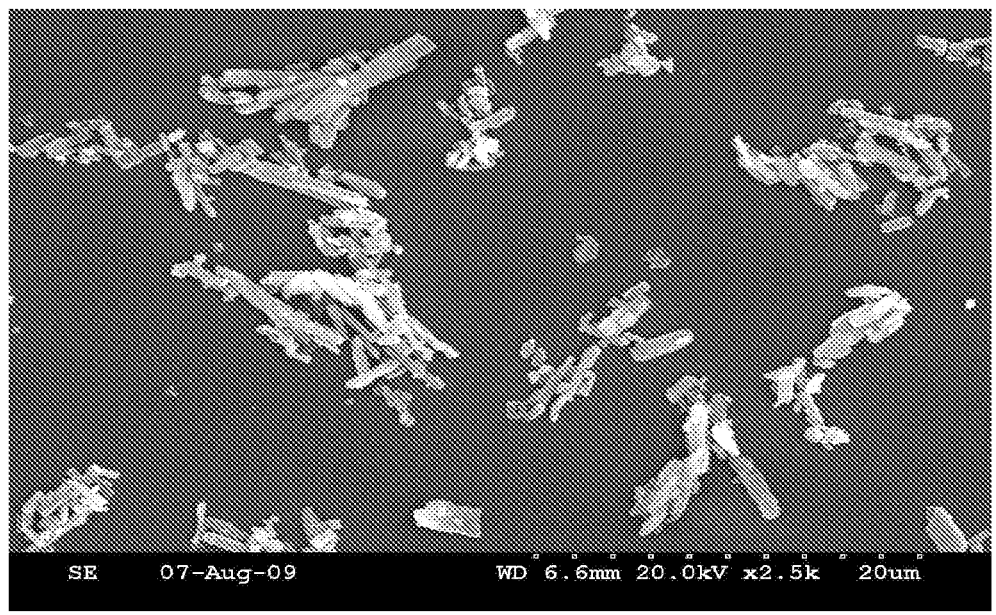
FIG. 2 is a micrograph of a comparative copper pyrithione.

Comparative Example A microscopic images for ACM (air classifying milling) copper pyrithione, available from Arch Chemicals, Inc. under trade name Copper Omadine is shown in FIG. 2. Scale at bottom right is from 0-20 microns. FIG. 2.

Example 3 and Comparative Example B

Settling Characteristics of the Copper Pyrithione Particles

Example 3

11% copper pyrithione was prepared from zinc pyrithione powder and copper hydroxide in situ in a silyl acrylate and xylene solution The sample was viewed for settling after two weeks.

Comparative Example B copper pyrithione powder prepared in the conventional manner was dispersed into the same silyl acrylate and xylene solution to a concentration of 11% copper pyrithione. The sample was visually inspected for settling after two weeks A visual comparison of Example 3 to Comparative Example B shows that the conventional copper pyrithione has settled more than the copper pyrithione formed in situ., in accordance with the present invention.

To further demonstrate the superior settling characteristics of the copper pyrithione formed in situ, the dispersions were diluted 50% with xylene so that the viscosity is very low, under 10 cps for both. After 24 hours, there is a substantial difference between the settling of the conventional copper pyrithione and that of copper pyrithione formed in situ, in accordance with the present invention Conventional milled copper pyrithione has settled by 22 mm. In situ generated copper pyrithione has settled only 7 mm in 24 hrs.

Example 4 and Comparative Example C

Particle Size Analysis by Laser Light Scattering

Both the conventionally milled copper pyritione (comparative example C) and the in situ generated copper pyrithione (Example 4) particles sizes were measure by laser light scattering. Measurements were taken with different sonication pretreatments to break up weak agglomerates. Sonication times were 0, 30, and 120 seconds. The results are shown in Table 1. The data show that the in situ generated particles are much bigger and broadly represented in a bimodal distribution.

TABLE 1

| Copper Pyrithione | Sonication time | Average particle size | % □ 5μ | % □ 10μ |
|---|---|---|---|---|
| Comparative Example C | 0 | 5.29 | 49.0 | 21.4 |
| Comparative Example C | 30 seconds | 5.28 | 49.0 | 21.2 |
| Comparative Example C | 120 seconds | 4.99 | 52.0 | 12.9 |
| Example 3 | 0 | 12.66 | 36.3 | 53.2 |
| Example 3 | 30 seconds | 11.32 | 37.0 | 52.8 |
| Example 3 | 120 seconds | 10.29 | 37.0 | 51.5 |

Stoke's law suggests that all things being equal that smaller spherical particles should settle slower in identical liquids. Since the much larger particles of the in situ generated copper pyrithione settle much slower, the conclusion is that the particles are very different from spherical. The SEM shows the particles to be flat acicular needles. The larger needles physically interfere with the settling of the particles compared to the conventional copper pyrithione.

Example 5

Crack Resistance of Paint Made with Copper Pyrithione

The longer copper pyrithione particles would be expected to better reinforce the paint film when compared to the shorter, smaller conventionally milled copper pyrithione particles. To determine this, antifouling paints were formulated from the same silyl acrylate polymer, but with either conventional copper pyrithione added or with copper pyrithione formed in situ by the present invention.

A silyl acrylate polymer solution was produced as in example 1 and paints were made from this polymer. First, mixtures (dispersions) of copper pyrithione and polymer were made, and the paints were made from these mixtures. All weights are in grams.

| Copper pyrithione dispersion A. | |
|---|---|
| Silyl acrylate solution, 50% | 100.0 |
| Zinc pyrithione 97% | 12.50 |

-continued

| Copper pyrithione dispersion A. | |
|---|---|
| $Cu(OH)_2$ | 4.16 |
| $NH_4OH$ | 1.50 |

$Cu(OH)_2$ is added slowly over 80 minutes under the shear of a 1" dispersing blade at 3000 rpm

| Copper Pyrithione Dispersion B. | |
|---|---|
| Silyl acrylate solution, 50% | 50.0 |
| Copper pyrithione 97% | 12.5 |

Mix for 20 minutes under shear of at 1" dispersing blade at 3000 rpm. Speed lowered then add;

| Silyl acrylate solution | 50.0 |
|---|---|

Paints were made from each of the above copper pyrithione dispersions.

| Paint A. | |
|---|---|
| Silyl acrylate/copper pyrithione dispersion A | 30.0 |
| Talc | 5.0 |
| Cuprous oxide | 50.0 |
| Bentone SD-2 | 0.50 |

The above ingredients were mixed for 20 minutes at 3000 rpm with 1" dispersing blade then the following components were added:

| Disparlon A650-20X polyamide wax | 4.00 |
|---|---|
| Xylene | 12.0 |

Mixing continued at 3000 rpm for 5 minutes, lower speed and then the following component was added:

| Silyl acrylate copper pyrithione mix A | 20.50 |
|---|---|

| Paint B. | |
|---|---|
| Silyl acrylate/copper pyrithione dispersion B | 30.0 |
| Talc | 5.0 |
| Zinc Oxide | 1.50 |
| Cuprous oxide | 50.0 |
| Bentone SD-2 | 0.50 |

The above ingredients were mixed for 20 minutes at 3000 rpm with 1" dispersing blade then the following components were added:

| Disparlon A650-20X polyamide wax | 4.00 |
|---|---|
| Xylene | 12.0 |

Mixing continued at 3000 rpm for 5 minutes, lower speed and then the following component was added:

| | |
|---|---|
| Silyl acrylate copper pyrithione mix B | 18.0 |

Both wet paints were then applied to separate Leneta charts using a bar (Bird) applicator to produce a wet film thickness of approximately 0.003 inches (75 microns). The paint films were allowed to dry for 7 days. Each sample was bent over a ¾ inch mandrel. The films were slowly bent over a 3 second interval over the mandrel. After bending, the surfaces of the paint films were visually examined for cracks. The paint film from the paint made with copper pyrithione of the present invention was free of cracking. The paint film from the paint made with conventionally produced copper pyrithione showed some degree of cracking.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A process of preparing a composition containing particles of copper pyrithione comprising:
    reacting zinc pyrithione with a copper salt in the presence of a non-reactive polymer or non-polymer binder,
    wherein from greater than 20 wt % to 90 wt % of the copper pyrithione particles have a particle size of greater than 10 microns as determined by laser light scattering using a particle size distribution analyzer.

2. The process of claim 1 wherein said copper salt is selected from the group consisting of copper hydroxide, copper carbonate, copper nitrate, copper sulfate, copper chloride, and combinations thereof.

3. The process of claim 1 wherein said copper salt is copper hydroxide.

4. The process of claim 1 wherein the polymer is silyl acrylate.

5. The process of claim 1 wherein the polymer is metal acrylates, polyvinyl chloride, copolymers of vinyl chloride, vinyl acetate, copolymers of vinyl acetate, acrylic copolymers, epoxy, alkyd, polyvinyl alcohol, cellulose ethers, acid functional acrylates, chitosan, or polyvinyl ethers.

6. The process of claim 1 wherein the non-polymer binder is selected from the group consisting of rosin, rosin derivatives, and combinations thereof.

7. The process of claim 1 wherein the particles are flat acicular needle-shaped.

* * * * *